United States Patent
Miyashiro

Patent Number: 6,030,361
Date of Patent: Feb. 29, 2000

[54] GASTROSTOMY APPARATUS

[76] Inventor: Augusto M. Miyashiro, 42 87th St., Brooklyn, N.Y. 11209

[21] Appl. No.: 09/236,181

[22] Filed: Jan. 25, 1999

[51] Int. Cl.[7] .................................................. A61M 29/00
[52] U.S. Cl. ............................................ 604/96; 604/523
[58] Field of Search ............................. 604/54, 96, 151, 604/175, 247, 268, 523

[56] References Cited

U.S. PATENT DOCUMENTS

| | | |
|---|---|---|
| 4,393,873 | 7/1983 | Nawash et al. . |
| 5,007,900 | 4/1991 | Picha et al. ............................. 604/106 |
| 5,084,014 | 1/1992 | Picha et al. . |
| 5,336,203 | 8/1994 | Goldhardt et al. . |
| 5,356,391 | 10/1994 | Stewart . |
| 5,358,488 | 10/1994 | Suriyapa . |
| 5,391,159 | 2/1995 | Hirsch et al. . |
| 5,413,565 | 5/1995 | Michels et al. . |
| 5,458,583 | 10/1995 | McNeely et al. . |
| 5,549,657 | 8/1996 | Stern et al. . |
| 5,591,128 | 1/1997 | Sithole ...................................... 604/96 |
| 5,716,347 | 2/1998 | Gibbs et al. . |
| 5,718,691 | 2/1998 | Russo . |
| 5,720,734 | 2/1998 | Copenhaver et al. . |
| 5,728,178 | 3/1998 | Buffington et al. . |

*Primary Examiner*—Wynn Wood Coggins
*Assistant Examiner*—Kevin C. Sirmons
*Attorney, Agent, or Firm*—William H. Eilberg

[57] ABSTRACT

A gastrostomy apparatus includes an elongated tube having an inflatable balloon at its distal end, the tube passing through a flexible hemisphere. A spacer, which can be another tube or sheath, surrounds the primary tube in the region between the hemisphere and the proximal end of the tube. When the tube has been inserted into the patient, the balloon is inflated, and the tube pulled back so that the balloon abuts the interior wall of the stomach. The hemisphere is positioned to abut the skin or the exterior of the abdominal wall, and the spacer is affixed to the tube so that the hemisphere cannot migrate towards the proximal end of the tube. The spring action of the hemisphere counteracts the peristaltic motions of the stomach, and tends to keep the apparatus in place. The apparatus thus reduces the likelihood of leakage of gastric contents, and thus minimizes the risk of infection at the gastrostomy site.

24 Claims, 6 Drawing Sheets

GASTROSTOMY APPARATUS

BACKGROUND OF THE INVENTION

This invention relates to the field of gastrostomy tubes, which are used to deliver nutrients and/or medications directly to the stomach of an infirm patient. The gastrostomy apparatus of the present invention includes means for preventing leakage of gastric contents, and for reducing or eliminating irritation of the skin adjacent to the gastrostomy site.

It has been known to use gastric tubes to administer essential nutrient solutions and medications to persons with severe dysphagia. The gastric tube is inserted through a hole, or gastrostomy, in the abdominal wall and the stomach wall. The terms "gastric tubes" and "gastrostomy tubes" are used interchangeably in this specification.

Gastric tubes typically include a balloon at the distal end. The balloon, when inflated, anchors the gastric tube within the stomach. Examples of prior art gastrostomy tubes which have balloons at their distal ends are shown in U.S. Pat. Nos. 5,358,488 and 5,458,583. The typical prior art gastrostomy device also includes a retention disk, or its equivalent, which remains on the outside of the gastrostomy. Thus, when the gastrostomy apparatus is in use, the abdominal wall and the wall of the stomach are sandwiched between the inflated balloon and the disk. The disk provides some resistance to the peristaltic motions of the stomach, and prevents the gastric tube from migrating too far into the stomach.

A gastrostomy will inherently exert a constricting force on a gastric tube inserted therethrough, and this constriction tends to prevent gastric contents from leaking out onto the surrounding skin. However, in some patients, the constrictive pressure of the gastrostomy channel is ineffective in preventing leakage. The leaked material, which may include a mixture of feeding solutions, dissolved or suspended medications, and gastric secretions, irritates the skin around the gastrostomy. The result is inflammation, ulceration, and sometimes infection. Thus, the gastrostomy must be continually monitored for leakage.

To minimize the harm from potential leakage of gastric contents, it is necessary to take special care that gastric tubes and their immediate environments are kept clean. The gastric tube itself must be regularly flushed with water, and the skin surrounding the gastrostomy opening must be kept clean and dry.

When leakage is noted, caregivers may react by inflating the balloon, if it is not already fully inflated, and/or by adjusting the retention disk so that it allows the balloon to be conveniently positioned against the stomach wall. Leakage may also be countered by reducing the volume and/or flow rate of feeding. In order to stop persistent leakage, physicians have resorted to the use of gastrostomy tubes having progressively larger diameters, or to the administration of antacids and/or H2 blockers. Various local treatments, such as creams, pastes, and dressings, have also been applied around the gastrostomy. Usually such efforts are effective, but sometimes the gastric leakage continues and contacts the skin under the dressings.

In those patients in which the gastrostomy channel does not effectively prevent leakage, the use of larger diameter tubes does not solve the problem. Moreover, inflammatory secretions in the vicinity of the gastrostomy lubricate the gastric tube and allow the retention disk to slide, thus allowing the gastric tube to move in an undesired manner. In particular, the peristaltic motions of the stomach draw the gastric tube further into the stomach, and prevent the balloon of the gastric tube from being held continuously against the stomach wall to plug the opening in the stomach.

Thus, neither the balloon nor the retention disk solves the problem of gastric leakage. A caregiver may attempt to stop the leakage by increasing the pressure of the balloon against the stomach wall, and by fixing the retention disk with tape or some other means to make it hold its position. But this procedure has its own risks. Sandwiching of the tissues between the balloon and the retention disk may result in ischemia or necrosis of the gastric wall, or of the skin compressed by the balloon on one side and by the retention disk on the other.

When the possibility of a serious skin infection is high, it may be necessary to remove the gastric tube to prevent further damage to the patient's skin. Removal of the gastric tube allows the gastrostomy to close, and the patient must then be fed by a nasogastric tube until the abdominal skin wounds have healed.

The present invention solves the above-described problems, by providing a gastrostomy apparatus which minimizes leakage, and which also minimizes the harm encountered if some leakage does occur.

SUMMARY OF THE INVENTION

In a preferred embodiment, the gastrostomy apparatus of the present invention includes an elongated tube, having fluid ports at its proximal end, and an inflatable balloon at its distal end. A flexible hemisphere is inserted over the tube, near the distal end, such that the tube passes through an opening in the hemisphere. A spacer extends between the proximal end of the tube and the hemisphere. The spacer prevents the hemisphere from migrating towards the proximal end of the tube. A retention disk may be positioned between the hemisphere and the spacer. The disk grasps the tube by friction, and tends to prevent unwanted movement of the hemisphere. Alternatively, the disk could be replaced by a collar or flange which forms part of the hemisphere.

In use, the spacer is partially removed from the tube, so that the hemisphere (and retention disk, if present) can be moved, temporarily, towards the proximal end of the tube. The tube is then inserted into the stomach, to the maximum extent possible, or nearly so. Then the balloon is inflated, and the tube pulled outward, until the inflated balloon abuts the interior wall of the stomach. The hemisphere (with the retention disk, if present) is then moved towards the distal end, by sliding it along the tube, so that the hemisphere abuts the surface of the skin. The spacer is returned to its original configuration on the tube, so as to prevent migration of the hemisphere and retaining disk towards the proximal end of the apparatus.

If necessary, the effective length of the spacer may be varied. The spacer can be shortened simply by cutting off a piece of it. The spacer can be lengthened by splicing a piece of material alongside the spacer, in a region between the distal end of the spacer and the hemisphere or retaining disk.

The gastrostomy apparatus inherently tends to prevent leakage, because it "rides" with the normal peristaltic motions of the stomach. When the stomach pulls the gastric tube inward, the hemisphere deforms, and its natural elasticity causes it to return to its original shape, thereby restoring the gastric tube to its original position. Slits on the hemisphere determine the degree of its elasticity. The hemisphere, on the outside, and the inflated balloon, on the inside, therefore tend not to become unduly separated.

The gastrostomy apparatus avoids the harmful effects caused by simultaneous pressure on the abdominal wall and stomach wall from two opposing sides. In the present invention, the diameter of the hemisphere is chosen to be larger than the diameter of the inflated balloon, so that the hemisphere presses on the exterior of the abdominal wall and stomach wall at points which do not correspond to the region where the balloon abuts the interior stomach wall.

The present invention therefore has the primary object of providing an improved gastrostomy apparatus.

The invention has the further object of reducing the likelihood of leakage near a gastrostomy tube.

The invention has the further object of minimizing the potential harm which may occur in the event of leakage around a gastrostomy.

The invention has the further object of providing a gastrostomy tube which can be adjusted periodically to accommodate changes in the thickness of the abdominal wall.

The invention has the further object of providing a gastrostomy apparatus, which reduces or eliminates the harmful effects due to compression of an area of tissue of the abdominal wall and stomach wall between the gastric balloon and the retention disk.

The invention has the further object of providing a gastrostomy apparatus which accommodates the natural peristaltic motions of the stomach.

The invention has the further object of providing a method of using a gastrostomy apparatus as described above.

The reader skilled in the art will recognize other objects and advantages of the present invention, from a reading of the following brief description of the drawings, the detailed description of the invention, and the appended claims.

DETAILED DESCRIPTION OF THE INVENTION

Figure 1:
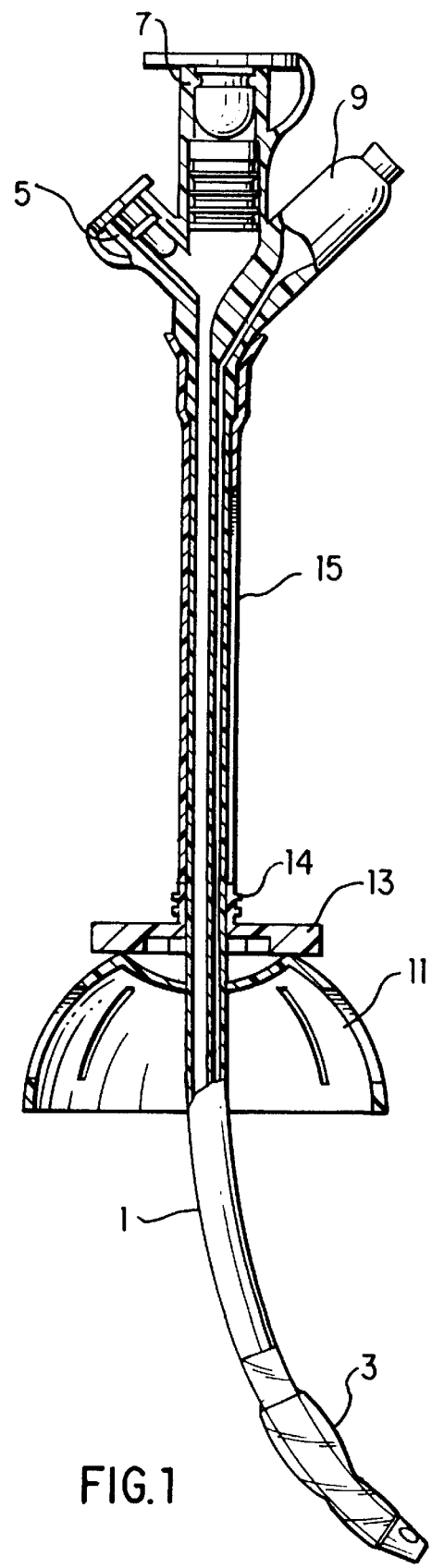
FIG. 1 shows a partial longitudinal cross-sectional view of the gastrostomy apparatus of the present invention.

FIG. 1 provides a partial longitudinal cross-sectional view of the gastrostomy apparatus of the present invention. The gastrostomy apparatus includes flexible gastrostomy tube 1 which has a balloon 3 near its distal end, and which is in fluid communication with ports 5, 7, and 9, near its proximal end. The balloon is shown in the uninflated condition in FIG. 1. Ports 5 and 7 are intended for use in supplying nutrients and/or medications to the stomach of the patient, and port 9 is intended to supply a fluid which inflates the balloon. The preferred inflation fluid is either sterile water or a saline solution. Other fluids, such as air, could be used instead, and the invention should not be deemed limited according to the fluid used. In the preferred embodiment, the large port (port 7) is used for feeding, and the smaller port (port 5) is used to supply medication. But the roles of the various ports can be changed, within the scope of the invention.

The gastrostomy apparatus also includes flexible hemisphere 11, which is threaded over tube 1. The hemisphere has an opening at or near its apex, so that the tube may be inserted through the opening. The gastrostomy apparatus also includes retaining disk 13, which is in frictional engagement with the tube, and which therefore prevents the hemisphere from migrating towards the proximal end of the tube. The disk is connected to a flange 14 which frictionally surrounds the tube. Alternatively, the disk could be provided without a flange.

FIG. 1 also shows spacer 15, which can be another tube or sheath, or a section thereof, surrounding tube 1. The spacer is preferably concentric with tube 1. The spacer occupies the region, along the exterior of tube 1, between the retaining disk and the ports at the proximal end. With the spacer installed, the hemisphere cannot migrate towards the proximal end, because it is blocked by the spacer. The spacer is important because, if gastric contents or gastric secretions leak out of the gastrostomy, these materials tend to lubricate the tube, and reduce the friction between the hemisphere and/or disk and the tube. Thus, in the event of such leakage, the hemisphere and/or disk are therefore more likely to migrate towards the proximal end of the tube. The spacer reduces the possibility of such unwanted migration.

In one embodiment, the spacer can be made simply from a flexible tube, made of rubber or other elastomeric material. For example, the spacer can be fashioned from the body of a Foley catheter. Other constructions are possible, within the scope of the invention. It is preferred that the spacer be made of a flexible material, to preserve the flexibility of the gastrostomy apparatus as a whole.

Figure 2:
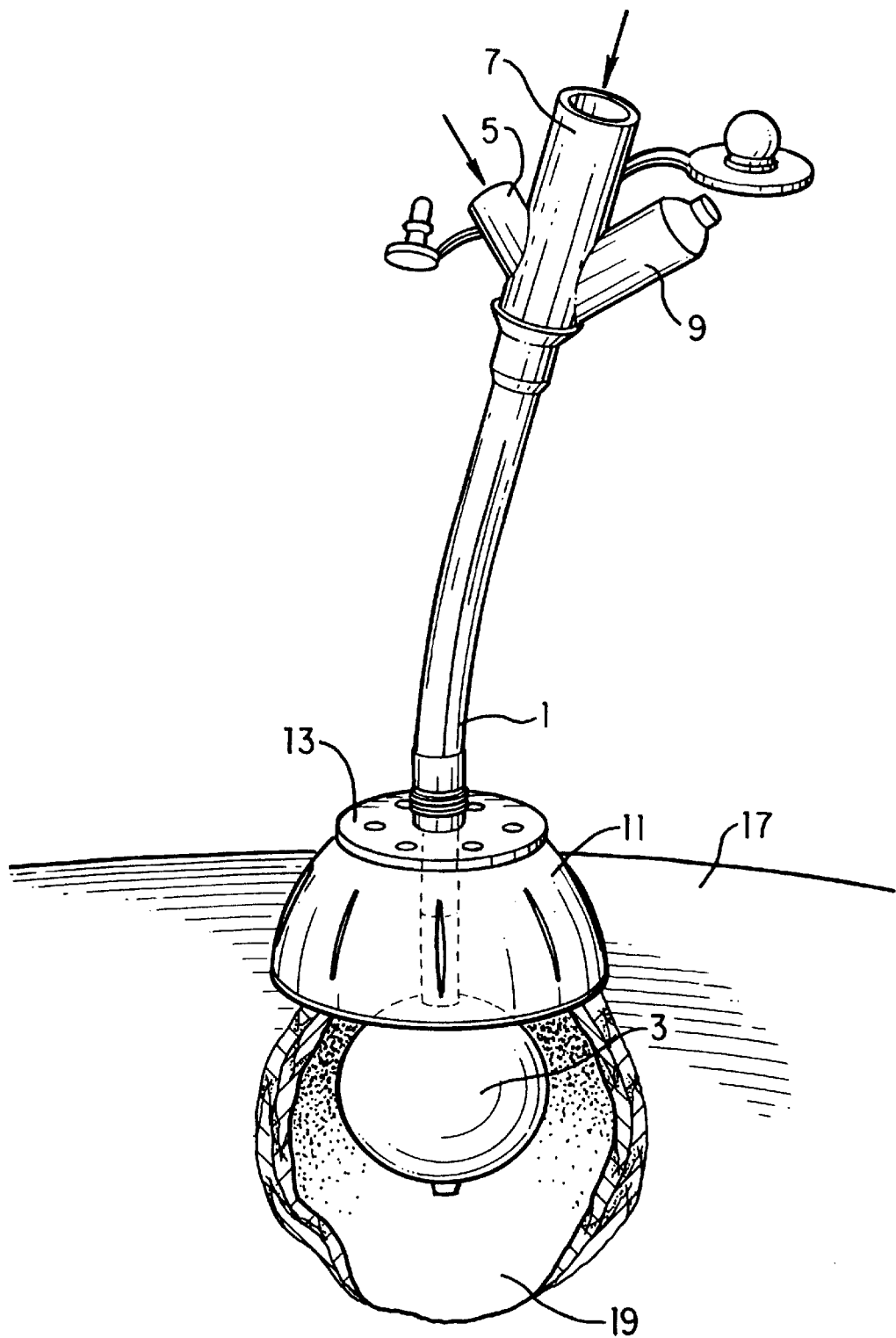
FIG. 2 provides an elevational view, with portions broken away, showing the gastrostomy apparatus of the present invention after it has been inserted into the stomach of a patient.

FIG. 2 shows the gastrostomy apparatus after it has been inserted into the stomach. In FIG. 2, the skin of the patient is identified by reference numeral 17, and the interior region of the stomach is denoted by reference numeral 19. As shown in FIG. 2, the gastrostomy tube 1 has been inserted into the stomach, and the balloon 3 has been inflated. The flexible hemisphere 11 remains on the exterior of the patient's skin. As can be seen in FIG. 2, the diameter of the inflated balloon is less than the diameter of the flexible hemisphere. FIG. 2 also symbolically indicates that medications and/or nutrients may be injected through ports 5 and 7. In one embodiment, the diameter of the inflated balloon is about 3 cm, and the diameter of the hemisphere is about 6 cm. The latter figures are illustrative only, and are not intended to limit the invention to any particular dimensions.

It is important that the diameter of the inflated balloon be kept less than the diameter of the hemisphere. With the above-described arrangement, the wall of the stomach and the abdominal wall are never pressed on two sides at the same position. Pressure on these tissues from two sides, at the same point, is potentially harmful, as it may lead to inflammation, and to death of tissues. With the apparatus of the present invention, the pressure exerted by the rim of the hemisphere, against the outside of the abdominal wall and stomach wall, does not directly oppose the pressure exerted by the balloon against the inside of the stomach wall.

Figure 3:
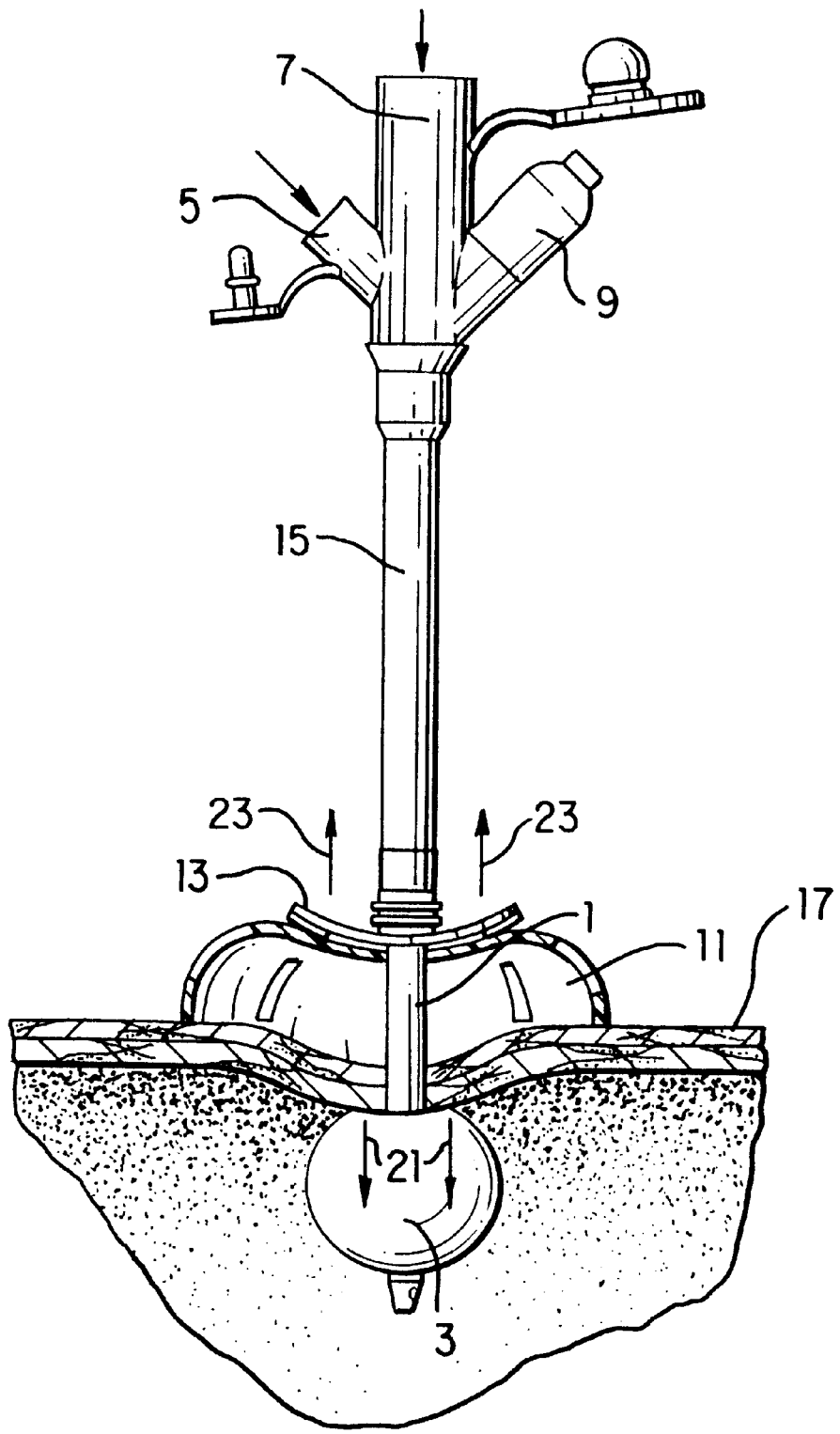
FIG. 3 shows the gastrostomy apparatus of the present invention, wherein the apparatus is being drawn towards the inside of the stomach by peristaltic motions, the figure showing how the flexible hemisphere tends to return the tube to its original position.

FIG. 3 illustrates the response of the gastrostomy apparatus of the present invention, to the normal peristaltic motions of the stomach. As shown in the figure, the stomach typically exerts a force on the gastrostomy tube, tending to pull the tube farther into the stomach, as indicated by arrows 21. The abdominal wall and stomach wall 17 are shown with a corresponding indentation, exaggerated for clarity of explanation. When the stomach pulls on the apparatus as shown by arrows 21, hemisphere 11 is made to flex, with its apex or dome being forced downward, also in the direction of arrows 21. When the hemisphere is deformed in this way, it tends to exert a spring force, seeking to return to its original condition. This spring force has the direction indicated by arrows 23, and therefore counteracts the inward force exerted by the stomach.

Figure 4:
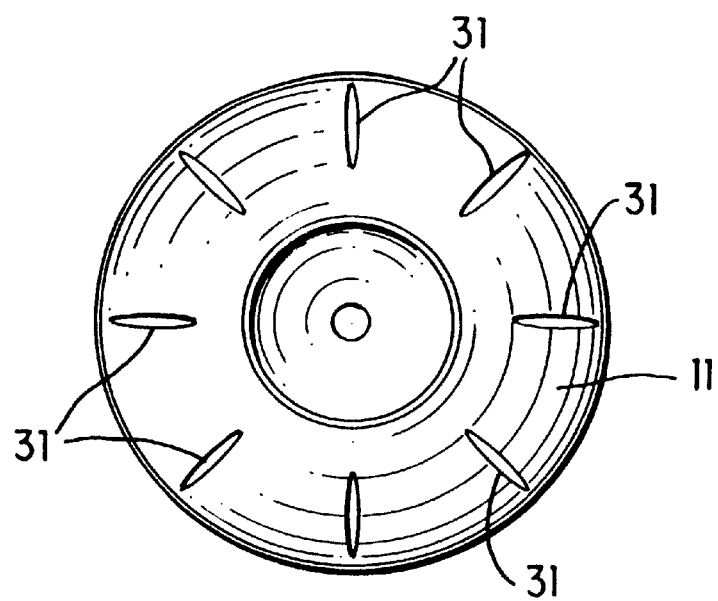
FIG. 4 provides a top view of the flexible hemisphere used in the present invention.

The structure of the hemisphere is shown, in a top view, in FIG. 4. As shown in FIG. 4, and in the other figures, the hemisphere 11 includes a plurality of slits 31, arranged around the sides of the hemisphere. These slits control the degree of stiffness of the hemisphere; the more numerous the slits, the less stiff the hemisphere becomes. The slits reduce the stiffness of the hemisphere, both by weakening the material of the hemisphere, and by allowing air to flow into and out of the hemisphere. The slits also have the beneficial effect of ventilating the area near the gastrostomy.

The number and position of the slits determines the spring force which the hemisphere exerts in response to peristaltic motions of the stomach. In one embodiment, it has been found that eight slits, disposed at equal angular positions around the circumference of the hemisphere, works well. Many other arrangements of slits are possible, within the scope of the present invention.

Figure 5:
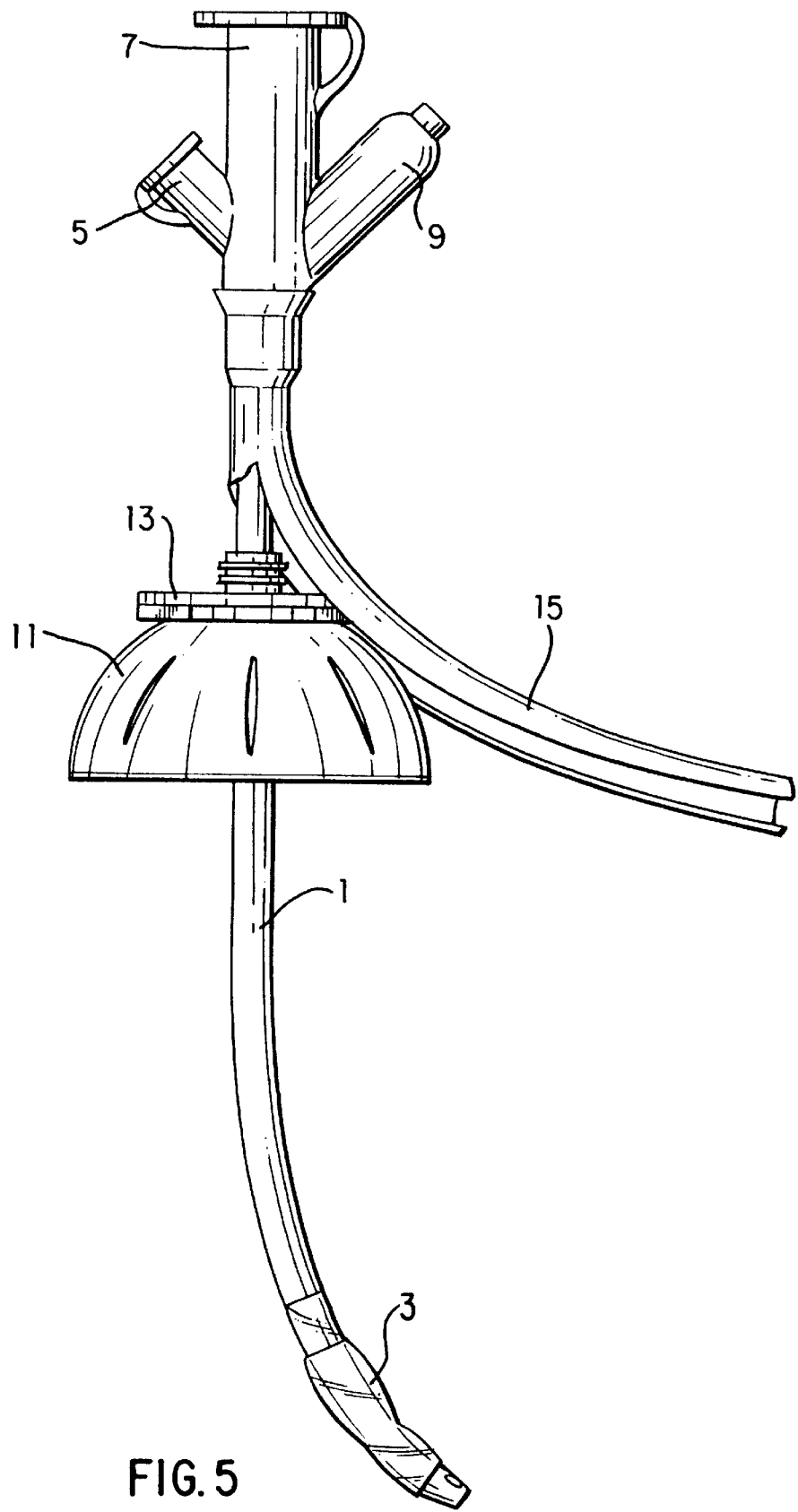
FIG. 5 provides an elevational view of the gastrostomy apparatus of the present invention, wherein the spacer forming part of the apparatus is peeled back to facilitate insertion of the gastrostomy tube into the stomach.

FIG. 5 shows the gastrostomy apparatus of the present invention at a time immediately before insertion into the stomach. Before inserting the gastrostomy tube, it is preferable to move the flexible hemisphere 11 and retaining disk 13 as far as practicable towards the proximal end, temporarily, so that the tube 1 can be inserted to the maximum depth possible. Inserting the tube to the maximum depth insures that the tube and balloon are fully within the stomach. It is important that the balloon be located within the stomach before it is inflated. In order to allow the hemisphere to be moved towards the proximal end, it is necessary to peel away a portion of spacer 15, as shown in FIG. 5. The spacer is therefore provided with a longitudinal slit, which extends along most, but not all, of its length. Since the proximal end of the spacer does not have a slit, the proximal end remains affixed to the tube when most of the spacer has been peeled away, as shown in FIG. 5.

After the tube has been inserted into the stomach, the balloon is inflated, and the tube is pulled back, until the inflated balloon abuts the interior wall of the stomach. The hemisphere and disk are moved towards the distal end, so that the hemisphere abuts the skin on the outside of the abdominal wall, and the balloon is located on the inside of the stomach. The spacer is then restored to its original position. The spacer can be secured with a surgical adhesive, or its equivalent, to keep it in the desired position surrounding tube 1.

Figure 6:
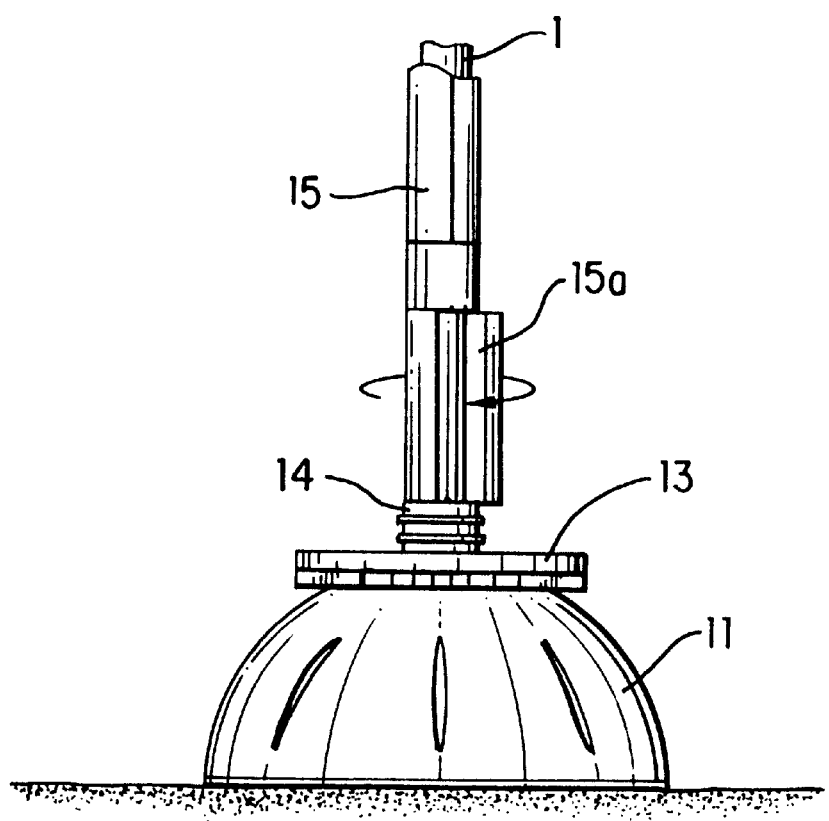
FIG. 6 provides an elevational view of a portion of the gastrostomy apparatus of the present invention, showing the insertion of an auxiliary spacer to increase the effective length of the primary spacer.

FIG. 6 illustrates a method and means for varying the effective length of the spacer. In FIG. 6, there is a gap between spacer 15 and flange 14 of disk 13. In this gap there is inserted auxiliary spacer material 15a; the figure shows this material being wrapped around the tube. The auxiliary spacer material can then be taped in position, so that it remains around the tube.

The length of the spacer may be reduced simply by cutting off a piece of the distal end of the spacer.

Figure 7:
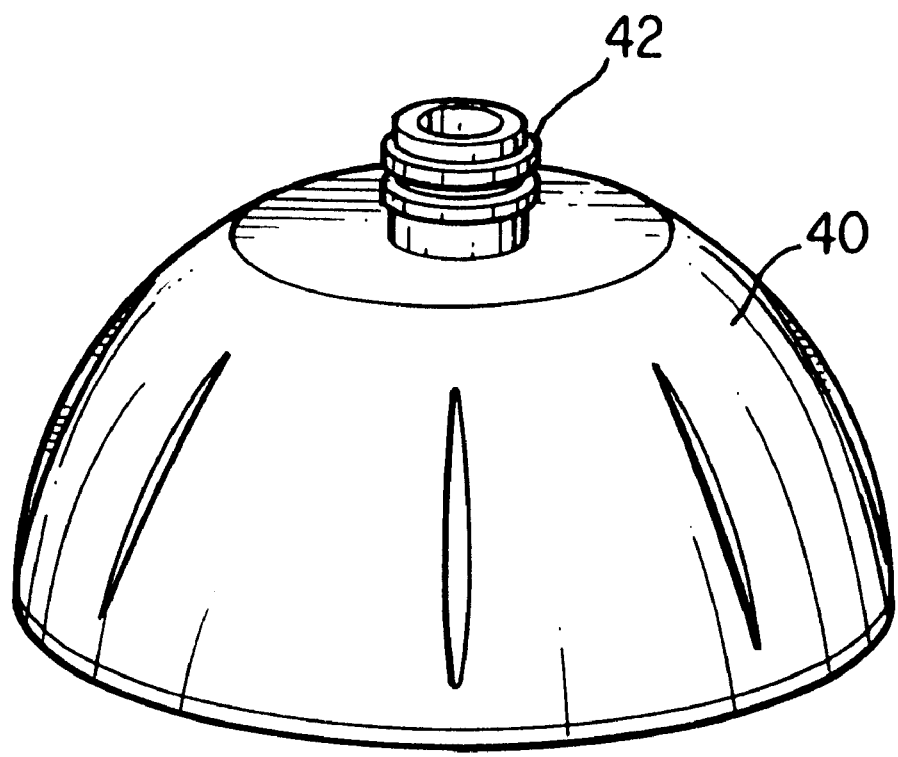
FIG. 7 provides a perspective view of a flexible hemisphere used in the present invention, made according to an alternative embodiment.

FIG. 7 shows an alternative embodiment, wherein the disk is eliminated. FIG. 7 shows a flexible hemisphere 40, which is of similar construction to that of the previous embodiment, but which includes flange 42. The flange has a size and shape that enables it to grip the tube frictionally, thus avoiding the need for a retaining disk. Other variations can be designed which also eliminate the disk.

The need for varying the effective length of the spacer arises from the following conditions. If the skin surrounding the gastrostomy becomes irritated or inflamed, due to leakage of gastric contents, the abdominal wall tends to become thicker in the regions of skin irritation. After the irritation or inflammation subsides, the abdominal wall returns to its normal thickness. This process may occur over several days. Thus, if the gastrostomy apparatus is inserted at a time when the abdominal wall is relatively thickened, and the thickness of the abdominal wall then decreases during the next several days, a space will develop, between the spacer and the hemisphere or disk. That is, the distal end of the spacer will no longer extend to the hemisphere or disk. In these conditions, the gastrostomy apparatus becomes loose, and the hemisphere may migrate into the region in which the spacer no longer extends.

The above-described problem is solved by sliding the hemisphere, with the disk, if it is present, towards the distal end, and then effectively lengthening the spacer, by adding an auxiliary spacer material as shown in FIG. 6, to compensate for this change in thickness of the abdominal wall. The change in thickness due to reduction of inflammation and swelling may typically be about one-half inch. Thus, in general, the length of the auxiliary spacer will be a small fraction of the length of the primary spacer.

There are other ways to vary the effective length of the spacer. One such alternative is to provide the spacer in the form of a hem. That is, a piece of the spacer, at its distal end, can be folded back over itself, thereby varying its effective length.

In use, the gastrostomy apparatus of the present invention maintains the balloon almost constantly against the stomach wall, with gentle tension. When the tube does migrate slightly into the stomach, due to peristaltic motions, the apparatus automatically counters this tendency, pulling the tube back to its original position when the peristaltic wave has passed.

The hemisphere can easily be everted temporarily, to facilitate the cleaning of the skin in the area of the gastrostomy. After such cleaning, the hemisphere can be easily returned to its original position.

The gastrostomy apparatus has been tested in patients, and has been found to work satisfactorily for 3–4 months without undue complications.

The invention can be further modified in various ways, as will be apparent to the reader skilled in the art. Such modifications should be considered within the spirit and scope of the following claims.

What is claimed is:

1. A gastrostomy apparatus comprising:

a) an elongated tube having a distal end and a proximal end, the proximal end including ports for connection to sources of fluid, the distal end including an inflatable balloon, b) a flexible hemisphere having an apex and having an opening at the apex, the hemisphere being inserted onto the tube such that the tube passes through said opening, and c) spacer means, extending along the tube from a vicinity of the hemisphere to a of said ports at the proximal end, wherein the spacer means comprises means for preventing the hemisphere from migrating towards the proximal end.

2. The gastrostomy apparatus of claim 1, further comprising a retaining disk disposed between the hemisphere and the spacer means, the disk comprising means for frictionally engaging the tube.

3. The gastrostomy apparatus of claim 1, wherein the spacer means comprises a tube section disposed concentrically around said elongated tube.

4. The gastrostomy apparatus of claim 1, wherein the spacer means includes a primary spacer and an auxiliary spacer, the auxiliary spacer being positioned adjacent the primary spacer.

5. The gastrostomy apparatus of claim 1, wherein the hemisphere includes a flange which comprises means for frictionally engaging the tube.

6. The gastrostomy apparatus of claim 1, wherein the hemisphere and the balloon are sized such that, when the balloon is inflated, the hemisphere has a diameter which is larger than a diameter of the balloon.

7. The gastrostomy apparatus of claim 1, wherein the hemisphere has a plurality of slits.

8. The gastrostomy apparatus of claim 1, wherein the hemisphere has a plurality of slits.

9. A gastrostomy apparatus comprising:

a) an elongated tube having a distal end and a proximal end, the proximal end including ports for connection to sources of fluid, the distal end including an inflatable balloon, and b) a flexible hemisphere having an opening, the tube being inserted through the opening of the hemisphere,
wherein the balloon, when inflated, has a diameter which is less than a diameter of the hemisphere,
further comprising spacer means, extending along the tube from the hemisphere to a base of said ports at the proximal end, wherein the spacer means comprises means for preventing the hemisphere from migrating towards the proximal end.

10. The gastrostomy apparatus of claim 9, further comprising spacer means, disposed on the tube between the hemisphere and the proximal end, wherein the spacer means comprises means for preventing the hemisphere from migrating towards the proximal end.

11. The gastrostomy apparatus of claim 10, further comprising a retaining disk disposed between the hemisphere and the spacer means, the disk comprising means for frictionally engaging the tube.

12. The gastrostomy apparatus of claim 10, wherein the spacer means comprises a tube section disposed concentrically around said elongated tube.

13. The gastrostomy apparatus of claim 10, wherein the spacer means includes a primary spacer and an auxiliary spacer, the auxiliary spacer being positioned adjacent the primary spacer.

14. The gastrostomy apparatus of claim 9, wherein the hemisphere includes a flange which comprises means for frictionally engaging the tube.

15. The gastrostomy apparatus of claim 9, wherein the hemisphere and the balloon are sized such that, when the balloon is inflated, the hemisphere has a diameter which is larger than a diameter of the balloon.

16. A method of inserting a gastrostomy apparatus into a patient, the apparatus including an elongated tube having a distal end and a proximal end, the proximal end including ports for connection to sources of fluid, the distal end including an inflatable balloon, a flexible hemisphere having an opening through which the tube passes, and a spacer extending along the tube from a vicinity of the hemisphere to a base of said ports at the proximal end, the method comprising the steps of:

a) removing at least part of the spacer from the tube, and sliding the hemisphere towards the proximal end, b) inserting the tube into a stomach of a patient, c) inflating the balloon, and pulling the tube until the balloon engages an inside wall of the stomach, d) sliding the hemisphere towards the distal end, so that the hemisphere contacts skin of the patient, and e) replacing the spacer so that the spacer extends to a base of said ports at the proximal end, and so that the hemisphere is prevented from migrating towards the proximal end.

17. The method of claim 16, wherein the spacer comprises a flexible sheath having a longitudinal slit which permits the sheath to be disengaged from the tube, and wherein step (a) comprises the step of peeling at least part of the sheath away from the tube.

18. The method of claim 17, further comprising the step of effectively lengthening the sheath by inserting an auxiliary spacer adjacent to the sheath.

19. A gastrostomy apparatus comprising:

a) an elongated tube having a distal end and a proximal end, the proximal end including ports for connection to sources of fluid, the distal end including an inflatable balloon, b) a flexible hemisphere having an apex and having an opening at the apex, the hemisphere being inserted onto the tube such that the tube passes through said opening, and c) spacer means, disposed on the tube between the hemisphere and the proximal end, wherein the spacer means comprises means for preventing the hemisphere from migrating towards the proximal end,
further comprising a retaining disk disposed between the hemisphere and the spacer means, the disk comprising means for frictionally engaging the tube.

20. A gastrostomy apparatus comprising:

a) an elongated tube having a distal end and a proximal end, the proximal end including ports for connection to sources of fluid, the distal end including an inflatable balloon, b) a flexible hemisphere having an apex and having an opening at the apex, the hemisphere being inserted onto the tube such that the tube passes through said opening, and c) spacer means, disposed on the tube between the hemisphere and the proximal end, wherein the spacer means comprises means for preventing the hemisphere from migrating towards the proximal end,
wherein the spacer means includes a primary spacer and an auxiliary spacer, the auxiliary spacer being positioned adjacent the primary spacer.

21. A gastrostomy apparatus comprising:

a) an elongated tube having a distal end and a proximal end, the distal end including an inflatable balloon, and b) a flexible hemisphere having an opening, the tube being inserted through the opening of the hemisphere, wherein the balloon, when inflated, has a diameter which is less than a diameter of the hemisphere, further comprising spacer means, disposed on the tube between the hemisphere and the proximal end, wherein the spacer means comprises means for preventing the hemisphere from migrating towards the proximal end, further comprising a retaining disk disposed between the hemisphere and the spacer means, the disk comprising means for frictionally engaging the tube.

22. A gastrostomy apparatus comprising:

a) an elongated tube having a distal end and a proximal end, the distal end including an inflatable balloon, and b) a flexible hemisphere having an opening, the tube being inserted through the opening of the hemisphere, wherein the balloon, when inflated, has a diameter which is less than a diameter of the hemisphere, further comprising spacer means, disposed on the tube between the hemisphere and the proximal end, wherein the spacer means comprises means for preventing the hemisphere from migrating towards the proximal end, wherein the spacer means includes a primary spacer and an auxiliary spacer, the auxiliary spacer being positioned adjacent the primary spacer.

23. A gastrostomy apparatus comprising:

a) an elongated tube having a distal end and a proximal end, the tube having a diameter, the distal end including an inflatable balloon, and b) a flexible hemisphere having an opening, the tube being inserted through the opening of the hemisphere, and c) a spacer, the spacer being concentric with the tube and having a length which is greater than the diameter of the tube, wherein the spacer comprises means for preventing the hemisphere from migrating towards the proximal end.

24. The gastrostomy apparatus of claim 23, wherein the length of the spacer is at least five times the diameter of the tube.

* * * * *